United States Patent [19]

Nagai et al.

[11] Patent Number: 4,838,276
[45] Date of Patent: Jun. 13, 1989

[54] BLOOD PRESSURE CUFF

[75] Inventors: Toshihiko Nagai; Tsuneo Nakagawa, both of Komaki, Japan

[73] Assignee: Nippon Colin Co., Ltd., Komaki, Japan

[21] Appl. No.: 127,369

[22] Filed: Dec. 2, 1987

[51] Int. Cl.$^4$ .............................................. A61B 5/02
[52] U.S. Cl. ..................................... 128/686; 128/327
[58] Field of Search ......... 128/686, 327, 672, 677-685

[56] References Cited

U.S. PATENT DOCUMENTS

| | | | |
|---|---|---|---|
| 2,113,534 | 4/1938 | Brown | 128/327 |
| 2,405,265 | 8/1946 | McAlpine | 128/686 X |
| 3,467,077 | 9/1969 | Cohen | 128/686 |
| 3,633,567 | 1/1972 | Sarnoff | 128/686 |
| 4,106,499 | 8/1978 | Ueda | 128/327 X |
| 4,149,540 | 4/1979 | Hasslinger | 128/327 |
| 4,353,374 | 10/1982 | Rebbe et al. | 128/327 X |
| 4,429,699 | 2/1984 | Hatschek | 128/686 X |
| 4,548,249 | 10/1985 | Slaughterbeck | 128/686 X |

Primary Examiner—Kyle L. Howell
Assistant Examiner—Angela D. Sykes
Attorney, Agent, or Firm—Matthews & Branscomb

[57] ABSTRACT

An improved blood pressure occlusion cuff which is easily attached to the patient's arm and which is comfortable for use over extended periods of time. The preferred embodiment of the invention blood pressure cuff comprises a flexible band, a buckle for releasably securing said band to a person's limb, structure for pressurizing said band to cause it to apply pressure to said limb and for sensing pressure variations related to the flow between said buckle and said limb when said band is secured to said limb.

6 Claims, 2 Drawing Sheets

BLOOD PRESSURE CUFF

FIELD OF THE INVENTION

The present invention relates generally to the field of blood pressure measurement systems. More specifically, the present invention provides an improved pressurizable occlusion cuff which is easily attached to the patient's arm and which is comfortable for use with repeated measurements.

BACKGROUND

One of the most common systems for obtaining an indirect indication of a patient's blood pressure is a system which measures pressure variations in a pressurized cuff placed on a patient's arm. Such a cuff is typically wrapped around the patient's arm and is pressurized while pressure variations or acoustic sounds relates to blood flow through a blood vessel are monitored to determined the patient's blood pressure.

Occlusion cuffs which have previously been available for such measurements are often difficult to attach the patient's arm and are often uncomfortable. In particular, it is very common to experience discomfort resulting from a portion of the skin in the arm becoming trapped in the fastening means used to secure the cuff to the arm. Such discomfort is especially acute when the cuff is used for an extended period of time.

SUMMARY OF THE INVENTION

The present invention overcomes the difficulties of the prior art by providing an improved blood pressure occlusion cuff which is easily attached to the patients' arm and which is comfortable for use over extended periods of time.

In the prefered embodiment, the improved blood pressure cuff comprises a flexible band, means for releasably securing said band to a person's limb, means for pressurizing said band to cause it to apply pressure to said limb and for sensing pressure variations related to the flow of blood in said limb and a shield connected to said band, said shield being positioned between said said securing means and said limb when said band is secured to said limb.

DETAILED DESCRIPTION OF THE PREFERRED EMBODIMENT

Figure 1:
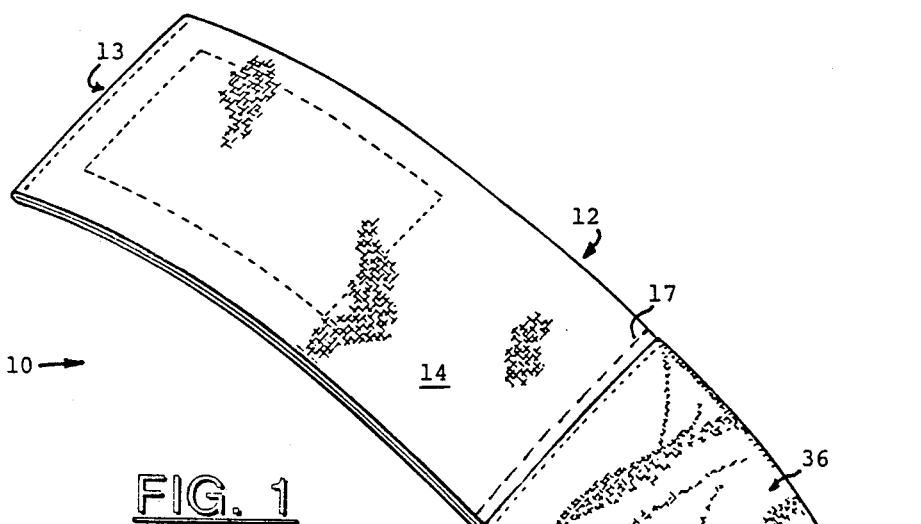
FIG. 1 is a plan view of one side of the preferred embodiment of the present invention.
Figure 2:
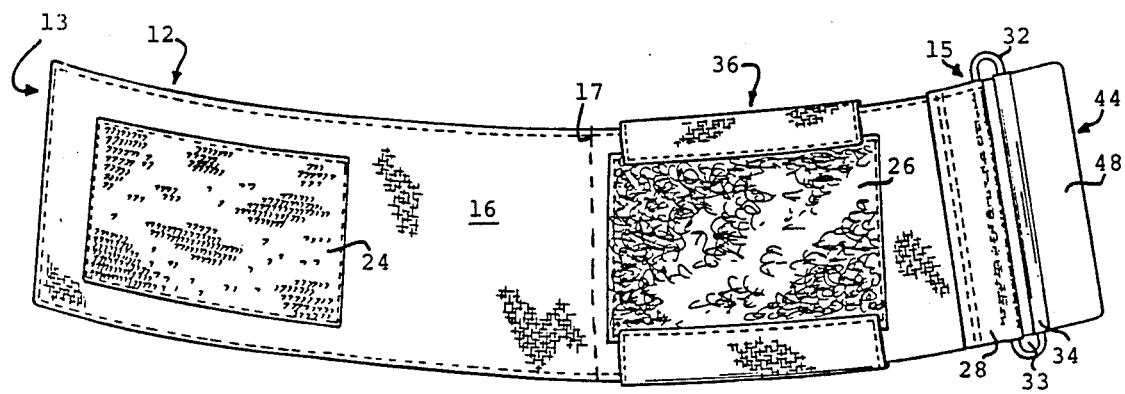
FIG. 2 is a plan view of the opposite side of the preferred embodiment of the present invention.

Referring to FIG. 1 and FIG. 2, the preferred embodiment of the blood pressure cuff of the present invention comprises an elongated, flexible band 12 having a first end 13 and a second end 15 opposite the first end 13. Band 12 is formed by pieces of fabric which are stitched together in a conventional manner so as to define a pair of opposed faces 14 and 16 and a cavity 18. Cavity 18 is located intermediate stitches 17 and 19 which are sewn across band 12 substantially transverse to the longitudinal axis of band 12. A conventional inflatable bladder (not shown) is located within pressure cavity 18 and is appropriately connected to a conventional tube bundle 22, which comprises a pneumatic tube for providing pressurized gas to said inflatable bladder and an electronic cable for transmitting electrical signals from pressure sensing transducers contained in said cavity. A zipper (not shown) is sewn or otherwise appropriately secured to band 12 to permit access to, and substantial enclosure of, cavity 18. As is further illustrated in FIG. 2, a patch of hooks 24 and a patch of loops or eyes 26 are sewn or otherwise appropriately connected to face 16.

Figure 3:
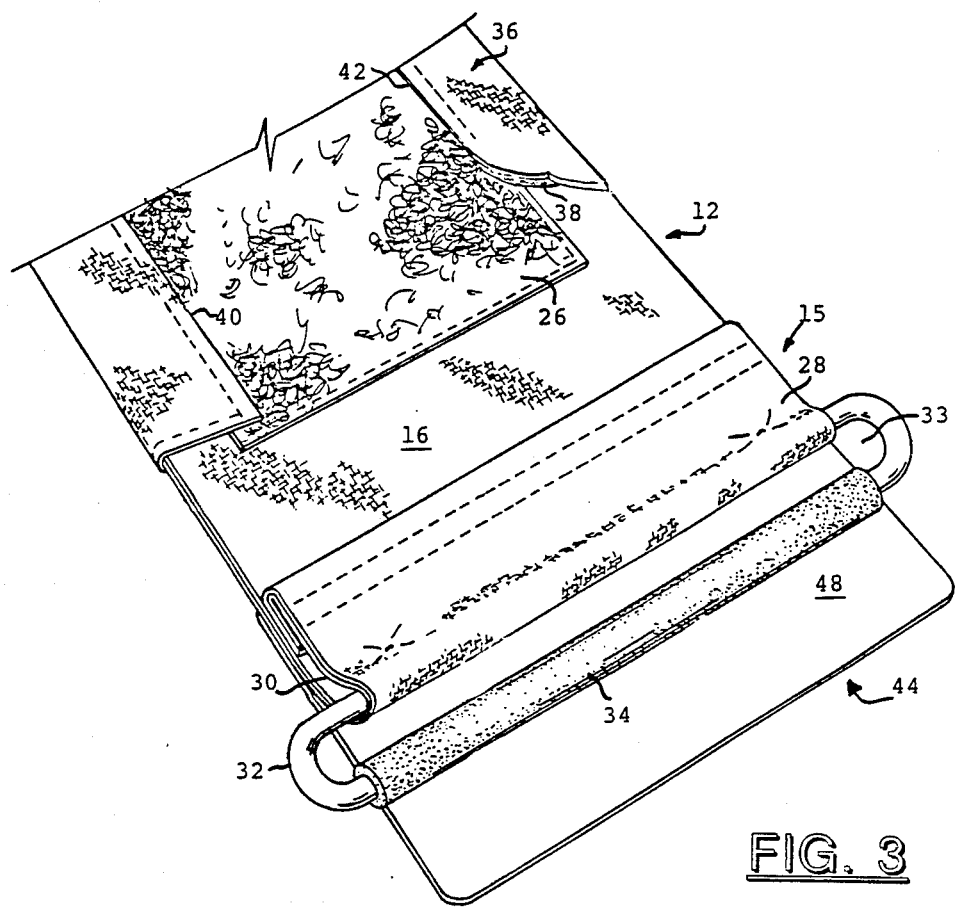
FIG. 3 is a partial perspective view of one end of the preferred embodiment of the present invention.

As illustrated in FIG. 2 and FIG. 3, the fabric forming band 12 is folded over and stitched to form a hem 28. Hem 28 defines a passage 30 which is adapted to receive one elongated side of a metal loop or buckle 32, which has a passage 33 therethrough. A rubber roller 34 is journaled for rotation about the elongated side of buckle 34 exterior to hem 28.

Referring again to FIGS. 1-3, the preferred embodiment of the blood pressure cuff of the present invention further comprises a protective cover 36. Cover 36 comprises a piece of flexible fabric having strips of hooks 38 which are stiched or otherwise appropriately connected to the inside of edges 40 and 42 of cover 36. Cover 36 is adapted to be positioned about band 12 so as to cover a portion of face 14 and may be removably secured to band 12 by the Velcro type closure formed by the mating engagement of hooks 38 and loops 26. The cover 26 substantially encircles the patient's arm A when the cuff is attached thereto.

Referring again to FIGS. 1-3, the preferred embodiment of the blood pressure cuff of the present invention further comprises a substantially rectangular flap or shield 44 which is stitched or otherwise appropriately connected to band 12 adjacent to hem 28. Shield 44 preferably comprises a substantially rigid elastic material having a first surface 46 and a second surface 48. The width of the shield 44 is substantially equivalent to the width of the band 12 and the length of shield 44 is sufficient to extend slightly beyond the distal end of band 12. In the preferred embodiment, the shield 44 extends approximately three fourths of an inch beyond band 12.

Figure 6:
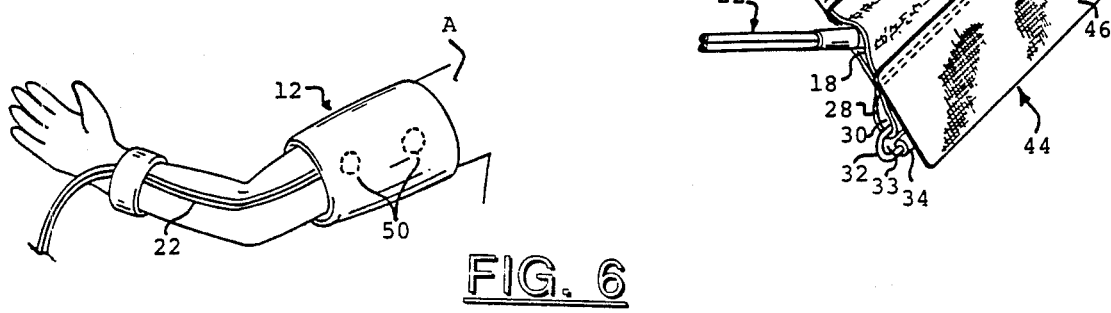
FIG. 6 is an elevational view illustrating the attachment of the preferred embodiment of the invention blood pressure cuff to a patient's arm.
Figure 4:
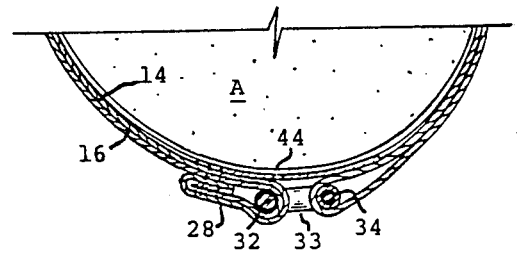
FIG. 4 is a partial cross-sectional view illustraitng details relating to the attachment of the preferred embodiment of the invention blood pressure cuff to a patient's arm.

Referring to FIG. 4 and FIG. 6, the attachment of the blood pressure cuff of the present invention to an arm A will be described in greater detail. The band 12 is preferably positioned adjacent to the arm A so that face 14 faces the arm A and sensors 50 located within cavity 18 are in proximity to the brachial artery within arm A. The first end of band 12 is thereafter inserted through passage 33 in the buckle 32 and is looped around roller 34. The first end of band 12 is thereafter pulled through buckle 32 so that band 12 is wrapped securely about arm A. The hooks 24 are thereafter pressed into mating engagement with loops 26 so as to removably secure the band 12 to arm A in a Velcry type closure.

Figure 5:
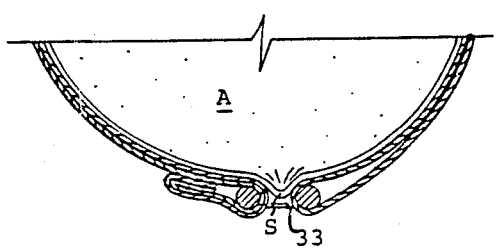
FIG. 5 is a partial cross-sectional view illustrating attachment of a blood pressure cuff without a shield to a patient's arm.

It is to be understood that shield 44 will be located intermediate to buckle 32 (and thus to the passage 33) and the arm A when the band 12 is secured to the arm A as described herein. The shield 44 thus prevents the skin of the patient's arm from being captured in the passage 33 of loop 32 as the band 12 is tightened. In the absence of the shield 44, the skin S underlying the passage 33 would be pinched within the passage, 33 as illustrated in FIG. 5, due to the compressing effect of the band 12 as it is tightened around the arm A. The first surface 46 of the shield 44 is preferably rough to prevent undesired slippage of the shield 44 against the skin once the cuff has been properly positioned. The second surface 48 is substantially smooth to facilitate movement of the band 12 through passage 33 when attaching the band 12 to the arm A.

Referring again to FIGS. 1-2, it can be seen that the band 12 has a slighly arcuate shape when in the fully extended position. Because of this shape of the band 12, the cuff will have a slightly tapered profile when attached to the patient's arm, as shown in FIG. 6. This provides a snug fit which conforms to the shape of the patient's arm.

While the blood pressure cuff of the present invention has been described in connection with the preferred embodiment, it is not intended to limit the invention to the specific form set forth herein, but on the contrary, it is intended to cover such alternatives, modifications and equivalents as may be included within the spirit and scope of the invention as defined by the appended claims.

We claim:

1. A blood pressure cuff, comprising:
   a flexible band of predetermined width and length, said length having a first end and a second end;
   buckle means formed of a closed loop of rigid material with two sides substantially straight for a distance greater than said band width for removably securing said band to a person one of said two sides being connected to said first end of said band;
   means secured within said band for applying pressure for sensing pulses; and
   shield means formed of a substantially rigid elastic material having a rough first surface and a smooth second surface connected to said first end of said band so as to be positioned intermediate said buckle means and said person when said band is in position to function as a blood pressure cuff.

2. The blood pressure cuff according to claim 1, further comprising a cover adapted to be releasably secured to said band.

3. The blood pressure cuff according to claim 2, wherein said cover comprises a piece of fabric having fastening means connected thereto adapted for mating engagement with fastener means connected to said band.

4. The blood pressure cuff according to claim 3, wherein said band has a slightly arcuate shape in the extended position and defining a cuff having a slightly tapered profile when secured to said person.

5. The blood pressure cuff according to claim 1, wherein said buckle means comprises a metal loop having a first elongated side and a second elongated side and wherein said first elongated side is received within a hem of said band.

6. The blood pressure cuff according to claim 1, wherein said buckle means further comprises a roller positioned about the other of said two sides of said loop.

* * * * *